US010183139B2

(12) United States Patent
Bonassa et al.

(10) Patent No.: US 10,183,139 B2
(45) Date of Patent: Jan. 22, 2019

(54) METHODS FOR CONTROLLING MECHANICAL LUNG VENTILATION

(71) Applicant: CareFusion 2200, Inc., San Diego, CA (US)

(72) Inventors: Jorge Bonassa, São Paulo (BR); Adriano De Lima Santos, São Paulo (BR); José Augusto Calvo Lonardoni, Itapevi (BR); Tito Coutinho Melco, São Paulo (BR)

(73) Assignee: Vyaire Medical Capital LLC, Yorba Linda, CA (US)

( * ) Notice: Subject to any disclaimer, the term of this patent is extended or adjusted under 35 U.S.C. 154(b) by 440 days.

(21) Appl. No.: 14/251,509

(22) Filed: Apr. 11, 2014

(65) Prior Publication Data
US 2015/0290409 A1    Oct. 15, 2015

(51) Int. Cl.
*A61M 16/00* (2006.01)
*A61M 16/20* (2006.01)
*A61M 16/08* (2006.01)

(52) U.S. Cl.
CPC ........ *A61M 16/205* (2014.02); *A61M 16/024* (2017.08); *A61M 16/0833* (2014.02);
(Continued)

(58) Field of Classification Search
CPC .......................... A61M 16/00–16/0012; A61M 16/0051–16/0084; A61M 16/0096;
(Continued)

(56) References Cited

U.S. PATENT DOCUMENTS

| 4,773,411 A | 9/1988 | Downs |
| 5,107,830 A | 4/1992 | Younes |

(Continued)

FOREIGN PATENT DOCUMENTS

| CN | 102711889 A | 10/2012 |
| CN | 103260682 A | 8/2013 |

(Continued)

OTHER PUBLICATIONS

International Search Report and Written Opinion for Application No. PCT/US2015/021589, dated Jun. 9, 2015, 11 pages.
(Continued)

*Primary Examiner* — Ned T Heffner
(74) *Attorney, Agent, or Firm* — Morgan, Lewis & Bockius LLP

(57) ABSTRACT

A method for controlling mechanical lung ventilation is described. The method may include supplying a breathing gas to an airway of a patient in an intermittent way such that a plurality of respiratory cycles are formed; measuring a volume received by the patient in one or more respiratory cycles of the plurality of respiratory cycles; comparing the measured volume of each of the one or more respiratory cycles with a user defined target volume; attributing a classifying score to each of the one or more respiratory cycles based at least partially on a deviation between the measured volume and the user defined target volume; summing the classifying scores and dividing the result by a sample size of the one or more respiratory cycles; attributing a pressure step value based at least partially on the division result; and adding the pressure step value to a present pressure.

10 Claims, 3 Drawing Sheets

(52) U.S. Cl.
CPC ............... *A61M 2016/003* (2013.01); *A61M 2016/0027* (2013.01); *A61M 2205/502* (2013.01); *A61M 2205/52* (2013.01)

(58) Field of Classification Search
CPC .................. A61M 16/04–16/0402; A61M 16/06–16/0661; A61M 2016/0015–2016/0042; A61M 2016/0413; A61M 2230/00; A61M 2230/005; A61M 2230/202–2230/205; A61M 2230/40–2230/46; A61M 16/22; A61B 5/082–5/097
See application file for complete search history.

(56) References Cited

U.S. PATENT DOCUMENTS

| | | | |
|---|---|---|---|
| 5,474,062 | A | 12/1995 | DeVires et al. |
| 5,582,163 | A | 12/1996 | Bonassa |
| 5,909,731 | A | 6/1999 | O'Mahony et al. |
| 6,369,114 | B1 | 4/2002 | Weil et al. |
| 7,246,618 | B2 | 7/2007 | Habashi |
| 7,810,497 | B2 | 10/2010 | Pittman et al. |
| 8,186,344 | B2 | 5/2012 | Bonassa |
| 8,408,203 | B2 | 4/2013 | Tham et al. |
| 8,677,999 | B2 | 3/2014 | Allum et al. |
| 8,876,728 | B2 | 11/2014 | Baloa Welzien et al. |
| 2002/0043264 | A1* | 4/2002 | Wickham ............ A61M 16/00 128/204.18 |
| 2005/0109340 | A1 | 5/2005 | Tehrani |
| 2006/0011195 | A1 | 1/2006 | Zarychta |
| 2007/0000494 | A1 | 1/2007 | Banner et al. |
| 2007/0199566 | A1 | 8/2007 | Be'eri |
| 2008/0072902 | A1 | 3/2008 | Setzer et al. |
| 2008/0295839 | A1 | 12/2008 | Habashi |
| 2008/0295840 | A1 | 12/2008 | Glaw |
| 2010/0218766 | A1 | 9/2010 | Milne |
| 2011/0232644 | A1 | 9/2011 | Doyle |
| 2012/0024286 | A1 | 2/2012 | Boring |
| 2012/0179061 | A1* | 7/2012 | Ramanan ............ A61B 5/087 600/538 |
| 2012/0216811 | A1 | 8/2012 | Kimm et al. |
| 2013/0074844 | A1 | 3/2013 | Kimm et al. |
| 2013/0125883 | A1 | 5/2013 | Bonassa et al. |
| 2015/0290407 | A1 | 10/2015 | Bonassa |
| 2015/0290408 | A1 | 10/2015 | Bonassa |

FOREIGN PATENT DOCUMENTS

| | | |
|---|---|---|
| WO | WO-2009039525 A2 | 3/2009 |
| WO | WO-2011089491 A1 | 7/2011 |
| WO | WO-2012085748 A1 | 6/2012 |
| WO | WO-2013175394 A1 | 11/2013 |

OTHER PUBLICATIONS

International Search Report and Written Opinion for Application No. PCT/US2015/021591, dated Jul. 1, 2015, 13 pages.
International Search Report and Written Opinion for Application No. PCT/US2015/021590, dated May 29, 2015, 15 pages.
Borello et al, "Modeling and Control of Systems for Critical Care Ventilation", American Control Conference, Jun. 2005, pp. 2166-2180.
Laubscher et al., "An Adaptive Lung Ventilation Controller," IEEE Transactions on Biomedical Engineering, Jan. 1994, vol. 41, No. 1, pp. 51-59.
Harris et al., "Continuous Monitoring of Lung Ventilation With Electrical Impedance Tomography", 1992 IEEE, pp. 1754-1755.
Chen et al., "Comparisons between Circle and Structural Models in Lung Ventilation Reconstruction by Electrical Impedance Tomography", 2008 IEEE, pp. 53-57.
Favre et al., "Closed-Loop Control of a Continuous Positive Airway Pressure Device", 2003 IEEE, pp. 419-422.
European Office Action for Application No. 15714363.7, dated Nov. 14, 2017, 5 pages.
Chinese Office Action for Application No. 201580024362.7, dated Jun. 5, 2018, 8 pages.

* cited by examiner

METHODS FOR CONTROLLING MECHANICAL LUNG VENTILATION

TECHNICAL FIELD

The present disclosure generally relates to providing lung ventilation assistance to patients requiring respiratory support, and more particularly to a method a method for controlling lung ventilation that is capable of providing pressure regulated respiratory cycles to achieve a target volume based on a number of delivered respiratory cycles.

BACKGROUND

A patient requiring lung ventilation support may be connected to a mechanical lung ventilator that applies a positive pressure to insufflate a volume mixture of air and oxygen to the lungs in an intermittent way (in cycles). For example, in an acute respiratory failure condition, the patient is typically sedated or in apnea state. In other words, there may be no spontaneous breathing effort and controlled cycles of mechanical ventilation may be required. Controlled cycles are generally volume or pressure controlled. Volume controlled cycles may have a fixed flow pattern and any variation of the respiratory mechanics may result in pressure change in the patient's airway. On the other hand, pressure controlled cycles generally keep pressure in the patient's airway constant, having free flow demand and, as a result, the volume may be variable.

SUMMARY

Aspects of the subject technology relate to a method capable of improving pressure regulated and volume control ventilation mode. In accordance with certain aspects, a method is provided for controlling artificial lung ventilation in a patient. The method can properly manage both conditions of no variability during acute phase of disease and natural variability observed in healthy human breathing, in order to provide volume requirements, patient comfort, and synchronization during all phases of ventilatory assistance.

In accordance with certain aspects, a method is provided for controlling artificial lung ventilation in a patient. The method can allow adequate and safe control of pressure to achieve volume requirements even in several degrees of patient breathing variability, avoiding detrimental lag and conflict between patient effort and/or lung mechanic changes and the ventilator response.

In accordance with certain aspects, a method is provided for controlling artificial lung ventilation in a patient. The method can adapt to the patient variability degree such that accommodations can be made for the respiratory variability of the patient.

In accordance with certain aspects, a method is provided for controlling artificial lung ventilation in a patient. The method can provide optimized performance and synchronization during both acute and weaning phase of ventilator assistance.

In accordance with certain aspects, a method is provided for controlling artificial lung ventilation in a patient. The method can allow manual and/or automatic control in order to adjust/adapt to the patient variability degree.

Various aspects of the subject technology may be achieved, for example, by a method for controlling mechanical lung ventilation, comprising the steps of: (i) supplying a breathing gas to the airway of a patient in an intermittent way, so as to form respiratory cycles; (ii) measuring a volume received by the patient in each respiratory cycle, during a sample size of respiratory cycles; (iii) comparing the measured volume of each respiratory cycle with a user defined target volume; (iv) attributing a classifying score to each respiratory cycle based on the deviation between the measured volume and the target volume; (v) summing the classifying scores and dividing the result by the actual sample size of respiratory cycles; (vi) attributing a pressure step value based on the previous division result; and (vii) adding the pressure step value to the present pressure. The pressure step can be a positive number or a negative number.

In certain embodiments, the respiratory cycles are controlled by pressure.

In certain embodiments, the actual sample size can be automatically calculated based on the measurement of variability of breathing. Particularly, in certain embodiments, the actual sample size is determined by first, calculating a Coefficient of Variation of a test sample size by the following equation:

$$CV = \frac{Std}{M},$$

where:
CV=Coefficient of Variation; and $$Std = \sqrt[2]{\sum \frac{(Vt - M)^2}{(Nt - 1)}},$$

where:
Vt=Tidal volume of each cycle;
M=Mean of all measured tidal volumes; and
Nt=Test sample size (number of cycles).

Second, attributing the actual sample size based on the calculated Coefficient of Variation and on the patient category, namely: neonatal, pediatric or adult.

In certain embodiments, the test sample size may be predetermined according to patient category, namely: neonatal, pediatric or adult.

In certain embodiments, the actual sample size is adjustable by the user according to the clinical evaluation of patient condition. Particularly, the actual sample size can be adjusted by the user based on the patient's inspiratory effort and associated variability.

In certain embodiments, the method may further comprise supplying a support pressure to the patient in a spontaneous breathing cycle, the support pressure being set in a Pressure Support Ventilation (PSV) mode of a ventilator.

In certain embodiments, the minimum and maximum values allowed to regulate pressure are defined by the user.

The subject technology is illustrated, for example, according to various aspects described below. Various examples of aspects of the subject technology are described as numbered clauses or embodiments (1, 2, 3, etc.) for convenience. These are provided as examples and do not limit the subject technology. It is noted that any of the dependent clauses may be combined in any combination with each other or one or more other independent clauses, to form an independent clause. The following is a non-limiting summary of some embodiments presented herein:

Clause 1. A method for controlling mechanical lung ventilation, the method comprising supplying a breathing gas to an airway of a patient in an intermittent way such that a plurality of respiratory cycles are formed; measuring a volume received by the patient in one or more respiratory cycles of the plurality of respiratory cycles; comparing the measured volume of each of the one or more respiratory cycles with a user defined target volume; attributing a classifying score to each of the one or more respiratory cycles based at least partially on a deviation between the measured volume and the user defined target volume; summing the classifying scores and dividing the result by a sample size of the one or more respiratory cycles; attributing a pressure step value based at least partially on the division result; and adding the pressure step value to a present pressure.

Clause 2. The method of clause 1 or any of the other clauses, wherein the sample size is automatically calculated based on the measurement of variability of breathing.

Clause 3. The method of clause 2 or any of the other clauses, further comprising calculating a Coefficient of Variation of a test sample size to determine the sample size by the following equation:

$$CV = \frac{Std}{M},$$

where:
CV=Coefficient of Variation; and $$Std = \sqrt[2]{\Sigma \frac{(Vt - M)^2}{(Nt - 1)}},$$

where:
Vt=Tidal volume of each cycle;
M=Mean of all measured tidal volumes; and
Nt=Test sample size (number of cycles).

Clause 4. The method of clause 3 or any of the other clauses, further comprising attributing the sample size based at least partially on the calculated Coefficient of Variation.

Clause 5. The method of clause 3 or any of the other clauses, further comprising attributing the sample size based at least partially on the calculated Coefficient of Variation and on a patient category.

Clause 6. The method of clause 5 or any of the other clauses, wherein the test sample size is predetermined according to the patient category, and wherein the patient category is one of neonatal, pediatric, or adult.

Clause 7. The method of clause 1 or any of the other clauses, wherein the sample size is adjusted by the user according to a clinical evaluation of patient condition.

Clause 8. The method of clause 7 or any of the other clauses, wherein the sample size is adjusted by the user based at least partially on the patient's inspiratory effort and associated variability.

Clause 9. The method of clause 1 or any of the other clauses, wherein the plurality of respiratory cycles are controlled by pressure.

Clause 10. The method of clause 1, wherein a minimum value and a maximum values allowed to regulate pressure are definable by the user.

Clause 11. A system for controlling mechanical lung ventilation, the system comprising: one or more processors; and a memory including instructions that, when executed by the one or more processors, cause the one or more processors to: supply a breathing gas to an airway of a patient in an intermittent way such that a plurality of respiratory cycles are formed; measure a volume received by the patient in one or more respiratory cycles of the plurality of respiratory cycles; compare the measured volume of each of the one or more respiratory cycles with a user defined target volume; and attribute a classifying score to each of the one or more respiratory cycles based at least partially on a deviation between the measured volume and the user defined target volume.

Clause 12. The system of clause 11 or any of the other clauses, wherein the instructions that, when executed by the one or more processors, further cause the one or more processors to: sum the classifying scores and dividing the result by a sample size of the one or more respiratory cycles; attribute a pressure step value based at least partially on the division result; and add the pressure step value to a present pressure.

Clause 13. The system of clause 12 or any of the other clauses, wherein the sample size is automatically calculated based on the measurement of variability of breathing.

Clause 14. The system of clause 13 or any of the other clauses, wherein the instructions that, when executed by the one or more processors, further cause the one or more processors to: calculate a Coefficient of Variation of a test sample size to determine the sample size by the following equation:

$$CV = \frac{Std}{M},$$

where:
CV=Coefficient of Variation; and $$Std = \sqrt[2]{\Sigma \frac{(Vt - M)^2}{(Nt - 1)}},$$

where:
Vt=Tidal volume of each cycle;
M=Mean of all measured tidal volumes; and
Nt=Test sample size (number of cycles).

Clause 15. The system of clause 14 or any of the other clauses, wherein the instructions that, when executed by the one or more processors, further cause the one or more processors to attribute the sample size based at least partially on the calculated Coefficient of Variation.

Clause 16. A machine-readable medium comprising instructions stored therein, which when executed by a machine, cause the machine to perform operations, the machine-readable medium comprising: instructions for supplying a breathing gas to an airway of a patient in an intermittent way such that a plurality of respiratory cycles are formed; instructions for measuring a volume received by the patient in one or more respiratory cycles of the plurality of respiratory cycles; instructions for comparing the measured volume of each of the one or more respiratory cycles with a user defined target volume; and instructions for attributing a classifying score to each of the one or more respiratory cycles based at least partially on a deviation between the measured volume and the user defined target volume.

Clause 17. The machine-readable medium of clause 16 or any of the other clauses, further comprising: instructions for summing the classifying scores and dividing the result by a sample size of the one or more respiratory cycles, instructions for attributing a pressure step value based at least partially on the division result; and instructions for adding the pressure step value to a present pressure.

Clause 18. The machine-readable medium of clause 17 or any of the other clauses, wherein the sample size is automatically calculated based on the measurement of variability of breathing.

Clause 19. The machine-readable medium of clause 18 or any of the other clauses, further comprising: instructions for calculating a Coefficient of Variation of a test sample size to determine the sample size by the following equation:

$$CV = \frac{Std}{M},$$

where:
CV=Coefficient of Variation; and $$Std = \sqrt[2]{\Sigma \frac{(Vt - M)^2}{(Nt - 1)}},$$

where:
Vt=Tidal volume of each cycle;
M=Mean of all measured tidal volumes; and
Nt=Test sample size (number of cycles).

Clause 20. The machine-readable medium of clause 19 or any of the other clauses, further comprising instructions for attributing the sample size based at least partially on the calculated Coefficient of Variation.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, drawings and detailed description are to be regarded as illustrative in nature and not as restrictive.

BRIEF DESCRIPTION OF THE DRAWINGS

The accompanying drawings, which are included to provide further understanding and are incorporated in and constitute a part of this specification, illustrate disclosed embodiments and together with the description serve to explain the principles of the disclosed embodiments. In the drawings.

DETAILED DESCRIPTION

Figure 1:
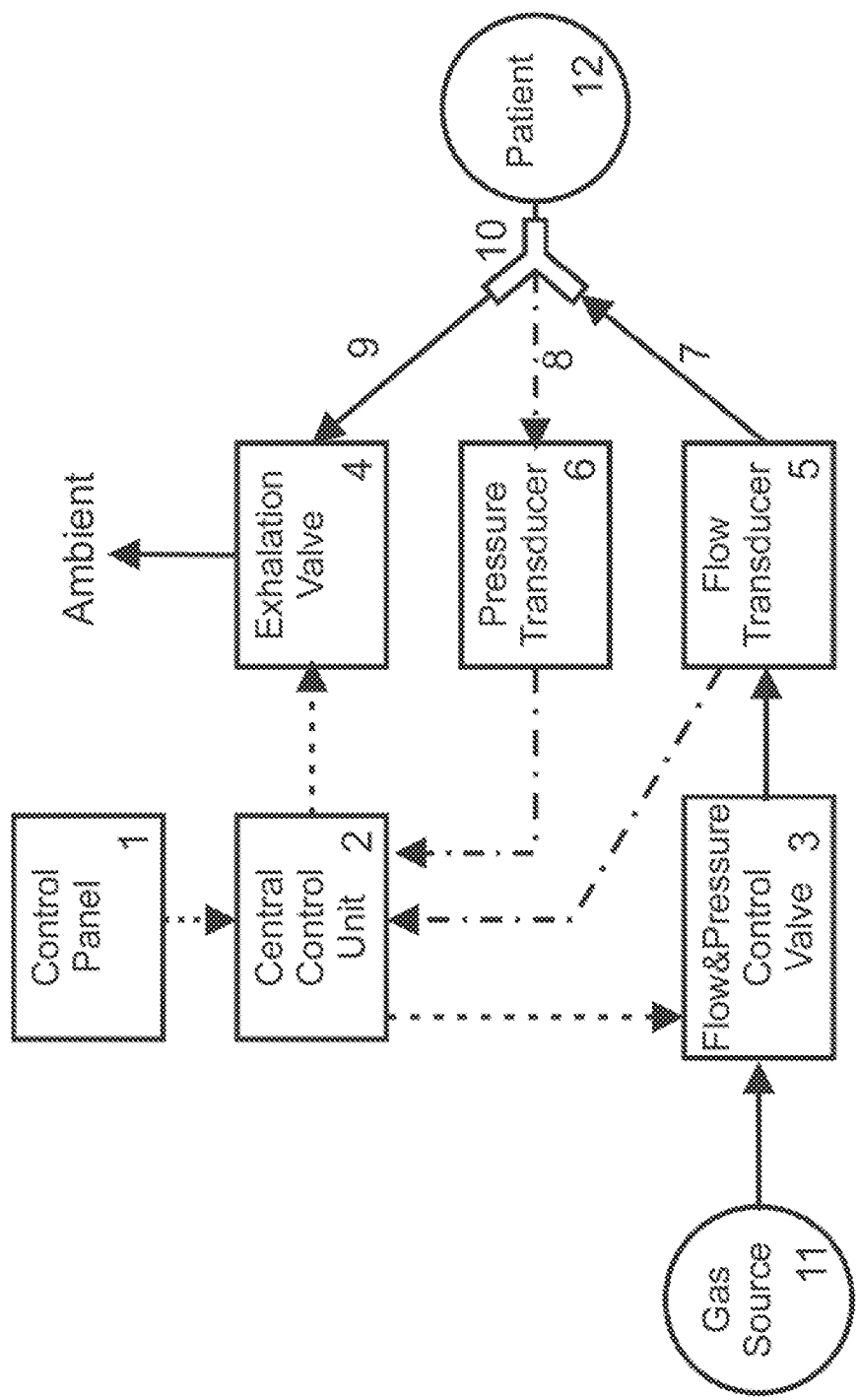
FIG. 1 is a schematic representation of an example of a lung ventilator connected to a patient, in accordance with aspects of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Initially, several example scenarios for providing lung ventilation assistance to patients requiring respiratory support will be described to compare and contrast other aspects of the present disclosure. For example, when a patient shows any inspiratory effort, cycles may be synchronized with his/her effort and then are designated as assisted cycles. Nevertheless, in this case, the volume controlled mode, despite being synchronized with the patient's initial effort, may not allow flow synchronism along the cycle, resulting in discomfort for the patient. In contrast, a pressure controlled mode may allow the patient to modulate the inspiratory flow, but is not seen to assure achieving the necessary tidal volume.

For example, in a stage when the patient has better control over ventilation, spontaneous cycles may be made available by the ventilator. Typically, these cycles may be partially assisted by the ventilator by means of a support pressure similar to the one used in the pressure controlled mode. However, in this case, the lack of control over the volume can be a critical point, particularly in patients at the beginning of the ventilator weaning.

In certain scenarios, Volume Assisted and Pressured Support (VAPS) mode cycles have assured a minimum volume, and in some cases, it may surpass the adjusted volume. Volume compensation on VAPS cycles may be obtained by means of a controlled flow by elevating pressure above the controlled pressure level, resulting in a mixed flow mode. In VAPS mode, volume compensation may occur at each cycle, resulting in a constant volume mode in all cycles, wherein pressure and volume will never be lower than the values adjusted by the operator, in accordance with some examples.

In other scenarios, Pressure Regulated Volume Controlled (PRVC) mode, which cycles are essentially pressure controlled can be uses, and based on the measurement of volume exhaled by the patient in the previous cycle, a ventilator may automatically adjust the pressure level required to reach the target volume. Although PRVC performs well in patients with weak or no inspiratory effort, it may not be adequate for a patient that has more effort and variability, for example. In such cases, the correction of pressure at each cycle can be more likely to contribute to patient dyspnea. For instance, if the patient inspires deeper in one cycle, as natural in normal breathing, during PRVC, the ventilator will decrease pressure in the next breath, increasing patient workload and possibly decreasing volume, as the patient returns to his/her initial effort level. Some clinical studies show an increased variability associated with an improved clinical condition, resulting in an asynchrony in PRVC as the patient's condition improves, which may be undesired.

Some example systems manage the variability adaptation of pressure regulated and volume control mode (PRVC), by considering the number of cycles in a one minute window for further pressure regulation. Such a system may allow the patient to maintain respiratory variability within a safe volume band. However, in some instances, a lower or higher variability degree may not be accommodated with a fixed period to get representative number of cycles. For example, a sudden change in lung compliance requires shorter periods for pressure adjustment than in the case of conditioning of respiratory muscles during weaning.

Figure 2:
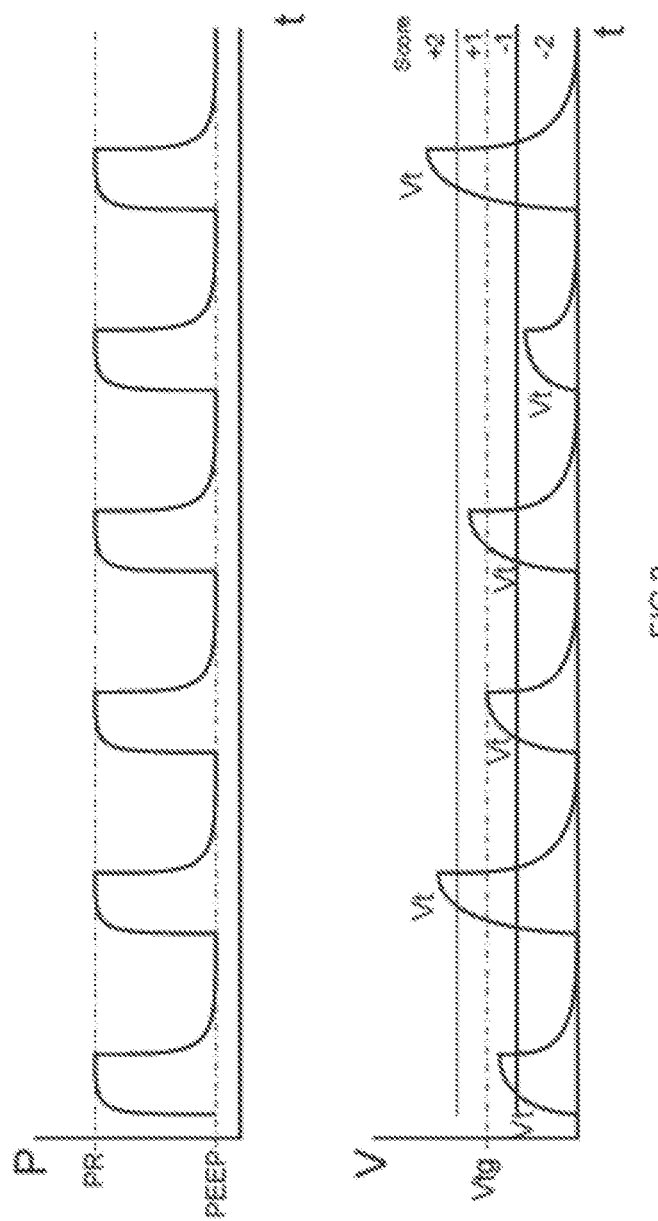
FIG. 2 is a graphical representation of pressure (P) and volume (V) curves for a hypothetic patient in a Pressure Control mode showing a patient's breathing variable pattern classified according to an example method of the present disclosure.

In view of the above examples, an example ventilator of FIG. 1 and graphical representation of FIG. 2 associated with an example method along with other aspects of the present disclosure will be descried.

FIG. 1 schematically illustrates an example ventilator system comprising a flow and pressure control valve 3 coupled to a source of gas 11. In certain embodiments, control valve 3 is capable of controlling the inspiratory flow by means of an inspiratory tube 7 coupled to a patient 12 by means of a "Y" type connector 10. The gas from the patient 12 may be exhaled through an exhalation tube 9 coupled to the other end of the "Y" connector 10. The exhaled gas may be controlled by an exhalation valve 4. The pressure in the airway of the patient 12 is sent from the "Y" connector 10, which is coupled to a pressure transducer 6 by means of a tube 8, for example.

In certain embodiments, the inspiratory flow may be measured by the flow transducer 5 positioned downstream from the flow and pressure control valve 3. Both inspiratory flow and airway pressure signals coming from flow transducer 5 and pressure transducer 6, respectively, together with parameters adjusted in the control panel 1, may be used by the central control unit 2 to control flow and pressure control valve 3 and exhalation valve 4.

In certain embodiments, flow and pressure 3 and exhalation 4 control valves are servo controlled by a microprocessor, but one or more of these valves may be activated by solenoids and/or pneumatics, for example.

The example ventilator system is capable of executing of methods of the present disclosure. However, the system is not limited to any particular arrangement and therefore, aspects of the system can be embodied in various alternatives. For example, the flow and pressure valve function may be performed by a compressor or turbine, in accordance with some embodiments. In other embodiments, the respiratory circuit may only comprise a single inspiratory branch and the function of the exhalation valve may be performed by a single orifice at the patient's connection. The inspiratory and/or pressure flow can be measured in different positions or even measured or estimated by different means, in accordance with some embodiments.

It is to be appreciated that aspects of the subject technology can be implemented in both ventilation systems intended for invasive ventilation and non-invasive ventilation, considering adjustments that may be required to compensate the volume of gas which is lost (e.g., in interfaces).

In certain embodiments, the example ventilator system may use a control unit that receives flow and pressure signals coming from respective transducers to control exhalation, flow and pressure values. From a control panel, the parameters values may be adjusted to control respiratory cycles. In certain configurations, the one or more of following control parameters may be required depending on the desired ventilatory strategy: Respiratory Frequency (FR); Sensitivity (S); Inspiratory Time (TI); Minimum Regulated Pressure (PRmin); Maximum Regulated Pressure (PRmax); and Sample Size (N). In other implementations, for example, one or more of the following control parameters may also be adjusted: Positive End Expiratory Pressure (PEEP); Inspired Fraction of Oxygen ($FiO_2$); Pressurization Rate or Pressure Slope; End Inspiratory Flow to finish the cycle.

In accordance with aspects of the subject technology, an example method for controlling mechanical lung ventilation may comprises a first step of monitoring (measuring) a tidal volume Vt received by the patient in each respiratory cycle, during a number of respiratory cycles adequate to get a representative sample size N (described in detail later in the present disclosure). Preferably, but not mandatory, the respiratory cycles are controlled by pressure. In the example of FIG. 2, six cycles (N=6) are illustrated.

Next, the example method may compare the volume of each cycle with a user (e.g., operator) defined target volume Vtg, and may classify (attributes) each cycle based on the deviation between the tidal volume Vt and the target volume Vtg, giving each cycle a score associated to the respective deviation band (in volume), as illustrated in the example of FIG. 2 (e.g., in the volume (V) curve), which represents a variable breathing pattern that results in different tidal volumes among respiratory cycles.

In accordance with certain embodiments, the following values of Table 1 are used with the example method:

TABLE 1

Relationship between Cycle Score and Deviation Band from target (in Volume).

| Cycle Score | Deviation Band |
| --- | --- |
| +2 | Vt > 1.2Vtg |
| +1 | 1.02Vt < Vt <= 1.2Vtg |
| 0 | 0.98Vtg =< Vt <= 1.02Vtg |
| −1 | 0.8Vtg =< Vt < 0.98Vtg |
| −2 | Vt < 0.8Vtg |

Although the values of the above table were obtained based on several experiments and clinical evaluation, it is to be understood that other values of cycle score and deviation band can be used, depending on the particular application or implementation.

In certain embodiments, the next step to be executed by the example method is to compute all cycle scores of sample size N as a sum of scores SSC divided by the sample size N. Based on the relation SSC/N, the example method defines (or attributes) a pressure step to be added to the actual regulated pressure PR, in order to distribute volume cycles equally in relation to the target volume Vtg. It is important to note that the pressure step may be either a positive or a negative number.

In accordance with certain embodiments, the following values of table 2 are used with the example method:

TABLE 2

Relationship between Pressure Regulated Step PRS and Ratio of the sum of scores SSC and the number of cycles of the sample size N.

| Pressure Step PRS | SSC/N |
|---|---|
| +4 | SSC/N < −1.5 |
| +2 | −1.5 =< SSC/N < −0.2 |
| 0 | −0.2 =< SSC/N <= 0.2 |
| −1 | 0.2 < SSC/N <= 1.5 |
| −3 | SSC/N > 1.5 |

Although the values of Table 2 above were obtained based on several experiments and clinical evaluation, it is to be understood that other values of pressure step and SSC/N band can be used, depending on the particular application or implementation, including fractionary numbers steps, for example.

In certain embodiments, the example method then regulates (or adjusts) pressure PR by adding calculated pressure step PRS and starts again the process of monitoring (measuring), comparing, computing and regulating (adjusting) pressure for the subsequent cycles.

In certain embodiments, the minimum and maximum values allowed to regulate pressure can be defined by the user in a control panel of the example ventilator.

In some embodiments, the sample size N will affect the frequency that pressure regulation will be performed during ventilation. For example, in a patient that presents a considerable degree of variability among the respiratory cycles, a small sample size N will result in inaccurate response, since pressure regulation will be applied based on only few cycles, which may not be representative of total patient breathing pattern. As a result, there will typically be a mismatch between ventilator and patient respiratory control. In contrast, if the patient shows no or small variability, which is a common state during acute phase of respiratory disease, the use of a large sample size will only delay response time in the event of a sudden change in respiratory mechanics, which is not unusual during mechanical ventilation.

In view of the above, in an embodiment, sample size N is a parameter that can be set/adjusted by the user according to the clinical evaluation of patient condition, more specifically, based on patient inspiratory effort and associated variability.

In other embodiments, the selection of sample size N is automated, and the example method takes in consideration the measurement of variability of breathing to track patient status. In this case, the method preferably calculates a Coefficient of Variation CV of a test sample size Nt and, based on calculated CV value, calculates the sample size N.

In certain embodiments, the Coefficient of Variation CV is calculated as the ratio of the Standard Deviation Std and mean of all measured tidal volumes M of a test sample size Nt, as provided below:

$$CV = \frac{Std}{M},$$

where:
CV=Coefficient of Variation; and
where:

$$Std = \sqrt[2]{\Sigma \frac{(Vt - M)^2}{(Nt - 1)}},$$

Vt=Tidal volume of each cycle;
M=Mean of all measured tidal volumes; and
Nt=Test sample size (number of cycles).

In certain embodiments, the following values of Table 3 (proved below) are used:

TABLE 3

Relationship between Coefficient of Variation CV and the sample size N, according to the patient category (adult, pediatric and neonate).

| CV (%) | N Adult Patients | N Pediatric Patients | N Neonate Patients |
|---|---|---|---|
| >50 | 15 | 20 | 30 |
| 40 < CV < 50 | 10 | 15 | 20 |
| 30 < CV < 40 | 5 | 10 | 15 |
| 20 < CV < 30 | 3 | 5 | 10 |
| <10 | 1 | 3 | 5 |

Although the values of the above table were obtained based on several experiments and clinical evaluation, it is to be understood that other values of Coefficient of Variation CV (%) and sample size N band can be used, depending on the particular application or implementation.

In certain embodiments, test sample size Nt is predetermined according to patient category. In other embodiments, several test sample sizes Nt may be used in order to verify the adequacy of coefficient of variation CV. For instance, all sample sizes in Table 3, for a specific patient category, can be tested to define which sample size matches with the calculated coefficient of variation CV.

In some instances, patient category is usually preset by the operator at the beginning of ventilation. Nevertheless, the patient category can also be detected by the example ventilator based on measured volumes and respiratory rate. For example, measured tidal volume (ml) multiplied by a factor of 6 (six) is a safe estimate of the ideal body weight (Kg) of the patient, so defining patient category.

Accordingly, the example method of the present disclosure is capable of controlling mechanical lung ventilation, providing pressure regulated cycles to achieve a target volume based on the measured volume in a number of previously delivered cycles. This number of cycles (e.g., sample size) can be adjusted manually by the operator or automatically by the ventilator to accommodate the respiratory variability degree of the patient. More specifically, the pressure of respiratory cycles may be regulated by the example method based on the volume measured in previous cycles in order to obtain posterior cycles with volumes at or around target volume, in such way that the distribution of these volumes is equally dispersed around the target volume or exactly at the target volume, depending on natural breathing variability of the patient.

In this regard, aspects of the subject technology are capable of properly managing both conditions of no variability during acute phase of disease and natural variability observed in healthy human breathing, so as to provide the volume requirements, patient comfort, and synchronization during all phases of ventilatory assistance, avoiding detrimental lag and conflict between patient effort and/or lung mechanic changes and the ventilator response. Thus, the example method of the present disclosure provides an optimized performance and synchronization during both acute and weaning phase of ventilator assistance.

In accordance with various aspects of the subject technology, an example method may be performed for controlling mechanical lung ventilation. The example method may comprise the steps of: supplying a breathing gas to the airway of a patient in an intermittent way, so as to form respiratory cycles; measuring a volume received by the patient in each respiratory cycle, during an actual sample size of respiratory cycles; comparing the measured volume of each respiratory cycle with a user defined target volume; attributing a classifying score to each respiratory cycle based on the deviation between the measured volume and the target volume; summing the classifying scores and dividing the result by the actual sample size of respiratory cycles; attributing a pressure step value based on the previous division result; and adding the pressure step value to the present pressure.

In some aspects, the actual sample size is automatically calculated based on the measurement of variability of breathing.

The example method may further comprise a step of calculating a Coefficient of Variation of a test sample size to determine the actual sample size by the following equation:

$$CV = \frac{Std}{M},$$

where:
CV=Coefficient of Variation; and $$Std = \sqrt[2]{\Sigma \frac{(Vt - M)^2}{(Nt - 1)}},$$

where:
Vt=Tidal volume of each cycle;
M=Mean of all measured tidal volumes; and
Nt=Test sample size (number of cycles).

The example method may further comprise a step of attributing the actual sample size based on the calculated Coefficient of Variation.

The example method may further comprise a step of attributing the actual sample size based on the calculated Coefficient of Variation and on the patient category, namely: neonatal, pediatric or adult.

In some aspects, the test sample size is predetermined according to patient category, namely: neonatal, pediatric or adult.

In some aspects, the actual sample size is adjusted by the user according to the clinical evaluation of patient condition.

In some aspects, the actual sample size is adjusted by the user based on the patient's inspiratory effort and associated variability.

In some aspects, the respiratory cycles are controlled by pressure.

In some aspects, the minimum and maximum values allowed to regulate pressure are defined by the user.

Figure 3:
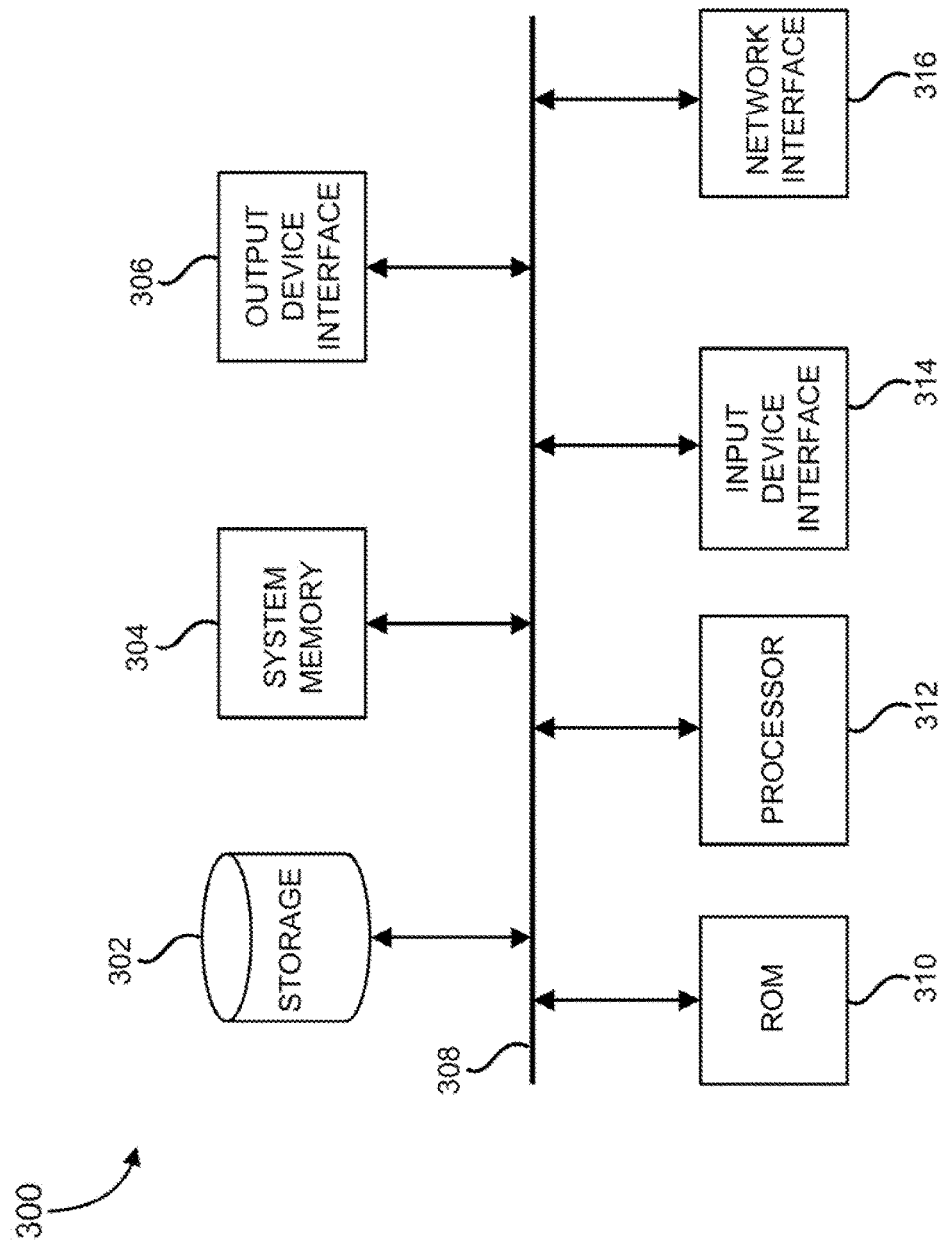
FIG. 3 conceptually illustrates an electronic system with which some aspects of the subject technology can be implemented.

FIG. 3 conceptually illustrates electronic system 300 with which implementations of the subject technology can be implemented. Electronic system 300, for example, can be, or can include, any of the control panel 1, the central control unit 2, a server, a desktop computer, a laptop computer, a tablet computer, a base station, or generally any electronic device. Such an electronic system includes various types of computer readable media and interfaces for various other types of computer readable media. Electronic system 300 includes bus 308, processing unit(s) 312, system memory 304, read-only memory (ROM) 310, permanent storage device 302, input device interface 314, output device interface 306, and network interface 316, or subsets and variations thereof.

Bus 308 collectively represents system, peripheral, and chipset buses that communicatively connect the numerous internal devices of electronic system 300. In one or more implementations, bus 308 communicatively connects processing unit(s) 312 with ROM 310, system memory 304, and permanent storage device 302. From these various memory units, processing unit(s) 312 retrieves instructions to execute and data to process in order to execute the processes of the subject disclosure. The processing unit(s) can be a single processor or a multi-core processor in different implementations.

ROM 310 stores static data and instructions that are needed by processing unit(s) 312 and other modules of the electronic system. Permanent storage device 302, on the other hand, is a read-and-write memory device. This device is a non-volatile memory unit that stores instructions and data even when electronic system 300 is off. One or more implementations of the subject disclosure use a mass-storage device (such as a magnetic or optical disk and its corresponding disk drive) as permanent storage device 302.

Other implementations use a removable storage device (such as a floppy disk, flash drive, and its corresponding disk drive) as permanent storage device 302. Like permanent storage device 302, system memory 304 is a read-and-write memory device. However, unlike storage device 302, system memory 304 is a volatile read-and-write memory, such as random access memory. System memory 304 stores any of the instructions and data that processing unit(s) 312 needs at runtime. In one or more implementations, the processes of the subject disclosure are stored in system memory 304, permanent storage device 302, and/or ROM 310. From these various memory units, processing unit(s) 312 retrieves instructions to execute and data to process in order to execute the processes of one or more implementations.

Bus 308 also connects to input and output device interfaces 314 and 306. Input device interface 314 enables a user to communicate information and select commands to the electronic system. Input devices used with input device interface 314 include, for example, alphanumeric keyboards and pointing devices (also called "cursor control devices"), touchpads, trackpads, or generally any device capable of receiving user input. Output device interface 306 enables, for example, the display of images generated by electronic system 300. Output devices used with output device interface 306 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touchscreen. In these implementations, feedback provided to the user can be any form of sensory feedback, such as visual feedback, auditory feedback, or tactile feedback;

and input from the user can be received in any form, including acoustic, speech, or tactile input.

Finally, as shown in FIG. 3, bus 308 also couples electronic system 300 to a network (not shown) through network interface 316. In this manner, the computer can be a part of a network of computers (such as a local area network ("LAN"), a wide area network ("WAN"), or an Intranet, or a network of networks, such as the Internet. Electronic system 300 may retrieve and/or receive information, e.g. via the network interface 316, from a cloud system, e.g. a cloud storage system. Any or all components of electronic system 300 can be used in conjunction with the subject disclosure.

In one or more implementations, the denominator and numerator of any ratio may be swapped, e.g. the ratio of two areas may be determined by dividing the first area by the second area or the second area by the first area. However, if the denominator and numerator of a ratio are swapped, the value of a threshold that the ratio is compared to may also be swapped accordingly.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

As used in this specification and any clauses of this application, the terms "computer", "server", "processor", and "memory" all refer to electronic or other technological devices. These terms exclude people or groups of people. For the purposes of the specification, the terms "display" or "displaying" means displaying on an electronic device.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

A phrase such as an "aspect" does not imply that such aspect is essential to the subject technology or that such aspect applies to all configurations of the subject technology.

A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but is to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A system for controlling mechanical lung ventilation, the system comprising:
   one or more processors; and
   a memory including instructions that, when executed by the one or more processors, cause the one or more processors to:
      supply a breathing gas to an airway of a patient in an intermittent way such that a plurality of respiratory cycles are formed;
      measure a volume received by the patient in each of the plurality of respiratory cycles;
      compare the volume of each of the plurality of respiratory cycles with a common user defined target volume that remains constant for the plurality of respiratory cycles;
      attribute a classifying score to each of the plurality of respiratory cycles, based at least partially on a deviation between the volume and the common user defined target volume, wherein the classifying score is one of a positive or a negative value indicative of a band of the deviation between the volume and the common user defined target volume; and
      select a sampling size of the plurality of respiratory cycles based on a patient inspiratory effort and a volume variability.

2. The system of claim 1, wherein the instructions that, when executed by the one or more processors, further cause the one or more processors to:
   sum the classifying scores and divide a resulting sum by the sample size of the plurality of respiratory cycles to obtain a division result;
   attribute a pressure step value based at least partially on the division result; and
   add the pressure step value to a present pressure.

3. The system of claim 2, wherein the sample size is automatically calculated based on a measurement of variability of breathing.

4. The system of claim 3, wherein the instructions that, when executed by the one or more processors, further cause the one or more processors to:
   calculate a Coefficient of Variation of a test sample size to determine the sample size by a following equation:

$$CV = \frac{Std}{M},$$

where:
CV=Coefficient of Variation; and $$Std = \sqrt[2]{\Sigma \frac{(Vt - M)^2}{(Nt - 1)}},$$

where:
Vt=Tidal volume of each cycle;
M=Mean of all measured tidal volumes; and
Nt=Test sample size (number of cycles).

5. The system of claim 4, wherein the instructions that, when executed by the one or more processors, further cause the one or more processors to attribute the sample size based at least partially on the Coefficient of Variation.

6. A machine-readable medium comprising instructions stored therein, which when executed by a machine, cause the machine to perform operations, the machine-readable medium comprising:
instructions for supplying a breathing gas to an airway of a patient in an intermittent way such that a plurality of respiratory cycles are formed;
instructions for measuring a volume received by the patient in each of the plurality of respiratory cycles;
instructions for comparing the volume of each of the plurality of respiratory cycles with a common user defined target volume that remains constant for the plurality of respiratory cycles;
instructions for attributing a classifying score to each of the plurality of respiratory cycles, based at least partially on a deviation between the volume and the common user defined target volume, wherein the classifying score is one of a positive or a negative value indicative of a band of the deviation between the volume and the common user defined target volume; and
selecting a sampling size of the plurality of respiratory cycles based on a patient inspiratory effort and a volume variability.

7. The machine-readable medium of claim 6, further comprising:
instructions for summing the classifying scores and dividing a resulting sum by the sample size of the plurality of respiratory cycles to obtain a division result;
instructions for attributing a pressure step value based at least partially on the division result; and
instructions for adding the pressure step value to a present pressure.

8. The machine-readable medium of claim 7, wherein the sample size is automatically calculated based on a measurement of variability of breathing.

9. The machine-readable medium of claim 8, further comprising:
instructions for calculating a Coefficient of Variation of a test sample size to determine the sample size by a following equation:

$$CV = \frac{Std}{M},$$

where:
CV=Coefficient of Variation; and $$Std = \sqrt[2]{\Sigma \frac{(Vt - M)^2}{(Nt - 1)}},$$

where:
Vt=Tidal volume of each cycle;
M=Mean of all measured tidal volumes; and
Nt=Test sample size (number of cycles).

10. The machine-readable medium of claim 9, further comprising instructions for attributing the sample size based at least partially on the Coefficient of Variation.

* * * * *